United States Patent [19]

Smiley

[11] Patent Number: 4,803,304

[45] Date of Patent: Feb. 7, 1989

[54] RECOVERY OF BIS(HEXAMETHYLENE)TRIAMINE

[75] Inventor: Robert A. Smiley, Wilmington, Del.

[73] Assignee: E. I. Du Pont de Nemours and Company, Wilmington, Del.

[21] Appl. No.: 38,659

[22] Filed: Apr. 15, 1987

[51] Int. Cl.$^4$ .............................................. C07C 85/26
[52] U.S. Cl. .................................... 564/498; 564/492; 564/512
[58] Field of Search ....................... 564/492, 498, 512

[56] References Cited

U.S. PATENT DOCUMENTS

| | | | |
|---|---|---|---|
| 2,987,452 | 6/1961 | Campbell et al. | 564/512 |
| 3,510,522 | 5/1970 | Larkin et al. | 564/498 |
| 3,523,973 | 8/1970 | Evans | 564/492 |
| 4,115,304 | 9/1978 | Chadwick | 564/492 |

Primary Examiner—Glennon H. Hollrah
Assistant Examiner—John A. Sopp

[57] ABSTRACT

Recovery of bis(hexamethylene)triamine from still heels of hexamethylenediamine by extraction using an aliphatic hydrocarbon having a boiling point between about 34° C. and 210° C.

5 Claims, No Drawings

RECOVERY OF BIS(HEXAMETHYLENE)TRIAMINE

FIELD OF THE INVENTION

This invention relates to a process for the isolation and purification of bis(hexamethylene)triamine, hereinafter sometimes referred to as "BHMT". BHMT has the chemical structure:

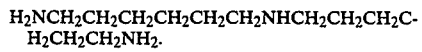

BACKGROUND OF THE INVENTION

BHMT is a byproduct from the manufacture of hexamethylenediamine. Large quantities of hexamethylenediamine are manufactured for use in the production of 6,6-nylon. It is conventional to separate the hexamethylenediamine from other reaction products by distillation. The distillation residue, still heels, contains varying amounts of BHMT, depending on how the plant is running. According to U.S. Pat. No. 4,115,304 to Chadwick, the distillation residue from one hexamethylenediamine plant contained the following amounts of the listed components:

| | |
|---|---|
| bis(hexamethylene)triamine | 5 to 40% by wt |
| C-10 diamine (primarily 1,4-di(aminomethyl)-1-ethyl cyclohexane) | 10 to 35% by wt |
| hexamethylene diamine and adiponitrile | 2 to 10% by wt |
| poly(hexamethylene)-polyamines and unknown compounds | 30 to 75% by wt |
| water | trace |
| ammonia | trace |

BHMT has been reported to have been recovered from such a residue by distillation: see U.S. Pat. No. 3,523,973 to Evans. However, because the BHMT has a high boiling point, attempts to separate it by distillation often lead to degradation and tar formation.

BHMT is useful as an additive in the manufacture of 6,6-nylon. It acts as a "branching agent", and according to U.S. Pat. No. 4,596,742 to Selivansky et al., in a sheath-core nylon yarn, wherein the sheath contains BHMT, the yarn has higher crimp development.

BHMT is also useful as an additive in 6,6-nylon polymers as a dye-receptor, can be added to asphalt to improve the bonding of the gravel to the other components, can be used in paper products, i.e., paper toweling, where it can replace diethylene triamine which acts to improve the wet strength of the paper products.

SUMMARY OF THE INVENTION

The present invention provides a process for the recovery of BHMT from hexamethylenediamine still heels, and comprises (1) contacting the still heels with an aliphatic hydrocarbon having a boiling point between about 34° C. and about 210° C., whereby the BHMT is extracted from the still heels and dissolved in the aliphatic hydrocarbon, (2) separating the aliphatic hydrocarbon containing the dissolved BHMT from the remaining components of the still heels, and then (3) separating the BHMT from the aliphatic hydrocarbon.

The step of contacting the aliphatic hydrocarbon with the still heels can be carried out at a temperature range below room temperature to the boiling point of the aliphatic hydrocarbon. Preferably the temperature is above about 20° C., with mixing to speed the extraction. The step of separating the aliphatic hydrocarbon containing the dissolved BHMT is best accomplished by decantation.

The step of separating the BHMT from the aliphatic hydrocarbon can be carried out by distilling the aliphatic hydrocarbon, or by cooling the aliphatic hydrocarbon containing the dissolved BHMT until the BHMT crystallizes from the solution, or the BHMT may be separated by extracting it from the aliphatic hydrocarbon with water, and subsequently evaporating the water.

DETAILED DESCRIPTION

Many suitable aliphatic hydrocarbons may be used to extract the BHMT from the hexamethylenediamine still heels, some are shown in the table below:

| | Distillation Range at 760 mm Hg °C. |
|---|---|
| Heptane | 94–98 |
| Hexane | 66–71 |
| Cyclohexane | 80–81 |
| Lacquer Diluent L | 97–107 |
| Mineral Spirits | 158–195 |
| Odorless Mineral Spirits | 179–198 |
| Pentane | 34–39 |
| Petroleum Ether | 35–60 |

EXAMPLE

Three hundred seventy grams of still heels of a commercial hexamethylenediamine plant containing 64% BHMT were continuously extracted with one liter of hexane for 6 hours, using an ether extraction apparatus, at room temperature. After 6 hours 240 grams of the still heels had gone into the hexane leaving 130 grams of BHMT-depleted residue.

The hexane-extract was distilled off at atmospheric pressure at about 71° C., and then the BHMT-rich residue was distilled through a short Oldershaw column at about 1 mm pressure. The initial product distilled (the foreshot) was about 42 grams. The foreshot was primarily 6-aminocapronitrile. The heart cuts were distilled at 50 to 152° C.—90 grams were collected which solidified on cooling. The product was analyzed and found to be bis(hexamethylene)triamine. The product had a melting point of 34° to 35° C.

BHMT can be recrystallized from hexane, or BHMT can be converted into a pourable white powder by melting distilled BHMT and pouring it slowly, with stirring, into cold hexane. The percipitate can then be filtered off and dried under vacuum.

I claim:

1. A process for the recovery of bis(hexamethylene)triamine from hexamethylenediamine still heels, which comprises (1) contacting the still heels with an aliphatic hydrocarbon having a boiling point between about 34° C. and about 210° C. whereby the bis(hexamethylene)triamine is extracted from the still heels and dissolved in the aliphatic hydrocarbon, (2) separating the aliphatic hydrocarbon containing the dissolved bis(hexamethylene)triamine from the remaining components of the still heels, and then (3) separating the bis(hexamethylene)triamine from the aliphatic hydrocarbon.

2. The process of claim 1 in which the bis(hexamethylene)triamine is separated from the aliphatic hydrocarbon by distillation of the aliphatic hydrocarbon.

3. The process of claim 1 in which the bis(hexamethylene)triamine is separated from the aliphatic hydrocarbon by crystallization.

4. The process of claim 1 in which the bis(hexamethylene)triamine is separated from the aliphatic hydrocarbon by extracting the bis(hexamethylene)triamine with water.

5. The process of claim 4 in which the aliphatic hydrocarbon is hexane.

* * * * *